United States Patent
Ehlis et al.

(10) Patent No.: US 6,217,856 B1
(45) Date of Patent: Apr. 17, 2001

(54) SYMMETRICAL TRIAZINE DERIVATIVES

(75) Inventors: Thomas Ehlis, Freiburg; Dietmar Hüglin, Eimeldingen; Helmut Luther, Grenzach-Wyhlen, all of (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/308,094

(22) PCT Filed: Nov. 10, 1997

(86) PCT No.: PCT/EP97/06226

§ 371 Date: May 17, 1999

§ 102(e) Date: May 17, 1999

(87) PCT Pub. No.: WO98/22447

PCT Pub. Date: May 28, 1998

(30) Foreign Application Priority Data

Nov. 20, 1996 (CH) .................................................. 2865/96

(51) Int. Cl.$^7$ ....................................................... A61K 7/06
(52) U.S. Cl. ............................. 424/70.9; 544/3; 544/187; 544/190; 424/70.1; 424/401
(58) Field of Search ................................. 544/187, 3, 190; 424/70.1, 70.9, 400, 401, 47, 59, 60

(56) References Cited

U.S. PATENT DOCUMENTS

| | | | | |
|---|---|---|---|---|
| 3,118,887 | * | 1/1964 | Hardy et al. | 260/248 |
| 3,932,402 | * | 1/1976 | Norell | 260/248 |
| 5,688,995 | * | 11/1997 | Luther et al. | 562/30 |
| 5,962,452 | * | 10/1999 | Haase et al. | 514/241 |
| 5,980,872 | * | 11/1999 | Luther et al. | 424/59 |
| 6,057,444 | * | 5/2000 | Haase et al. | 544/217 |

FOREIGN PATENT DOCUMENTS

| | | | |
|---|---|---|---|
| 614726 | * | 9/1962 | (BE) . |
| 539101 | * | 8/1973 | (CH) . |
| 542212 | * | 11/1973 | (CH) . |
| 743309 | * | 5/1995 | (EP) . |
| 659877 | * | 6/1995 | (EP) . |
| 0659877 | | 6/1995 | (EP) . |
| 0743309 | | 11/1996 | (EP) . |
| 97 03643 | * | 2/1997 | (WO) . |

OTHER PUBLICATIONS

Zhang et al, Chinese Chemical Letters, vol. 6, No. 10, pp. 839–842, "Cyclo–trimerization of nitriles by the active reactive alkai Metal Hydrides", 1995.*

Lang et al, Chem. Ber, vol. 106, pp. 2079–2081, "Notiz Zur Darstellung von arylsubstituierten Imidazolen", 1973.*

Llobera et al, Synthesis, vol. 85, No. 1, pp. 95–98, "Synthesis of S–Triazines from Aromatic Aldehydes", Jan. 1985.*

Stueber et al, J. Phys. Chem., vol. 99, pp. 10097–10109, "Ultraviolet Stabilizers of the 2–(2–hydroxyphenly)–1,3, 5–triazine Class: Structural and Spectro Scopic Characterization", 1995.*

Boyle et al, J. Chem. Soc, Perkins Trans. 1, vol. 76, No. 2, pp. 207–212, "The Reactions of Hydrazones and Related Compounds with Strong Bases", 1976.*

Rudenko et al., Zh. Org. Khim., 96, vol. 32, (10), pp. 1499–1521.

Zhang et al., Chin. Chem. Lett., 95, vol. 6, (10), pp. 839–842.

Stueber et al., J. Phys. Chem., 95, vol. 99, (25), pp. 10097–10109.

Llobera et al., Synthesis, 85, (1), pp. 95–98.

Boyle et al., J. Chem. Soc., Perkins Trans. 1, 76, (2), pp. 207–212.

Lang et al., Chem. Ber., 73, vol. 106, (6), pp. 2079–2081.

Ishikawa et al., Yuki Gosei Kagaku Kyokaishi, 67, vol. 25, (1), pp. 55–59.

* cited by examiner

*Primary Examiner*—Dameron L. Jones
(74) *Attorney, Agent, or Firm*—Kevin T. Mansfield

(57) ABSTRACT

A description is given of symmetrical triazine derivatives of formula (1), wherein $R_1$ and $R_2$ are each independently of the other hydrogen; $C_1$–$C_{12}$alkyl, $C_1$–$C_{12}$alkoxy; and $R_3$ is $C_1$–$C_{12}$alkyl; or $C_1$–$C_{12}$alkoxy. The easily accessible triazine derivatives are suitable for protecting ultraviolet-sensitive materials, in particular skin and hair of humans and animals, from the harmful effects of UV radiation.

(1)

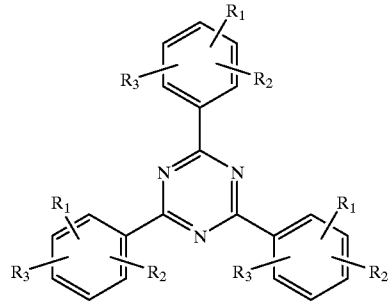

11 Claims, No Drawings

SYMMETRICAL TRIAZINE DERIVATIVES

This application is a 371 of PCT/EP97/06226 filed Nov. 10, 1997.

The present invention relates to symmetrical triazine derivatives, to the preparation of these compounds as well as to their use for protecting organic materials from the harmful effects of UV radiation.

O-alkylated o-hydroxyphenyltriazines (HPT) containing at least one o-hydroxyl group or at least two alkoxyphenyl substituents are known, e.g. from EP-A-0,743,309, as cosmetic UV absorbers having good spectral properties and good technical application properties. However, the preparation of such triazine derivatives, which are derived from the unsymmetrical basic structure

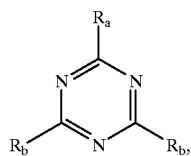

requires multistep synthesis processes.

In the above formula, $R_a$ and $R_b$ are a reactive radical, in particular a phenyl radical which is mono- or polysubstituted by hydroxyl groups.

Symmetrical triazine compounds which may be prepared from the symmetrical basic structure

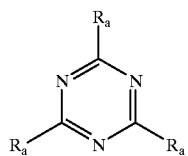

are easier to access in simple one-bach processes.

Such "triazine basic structures" may be prepared, for example, by trimerising corresponding benzonitrile compounds or, starting from cyanuric chloride, by Grignard reaction or Friedel-Crafts alkylation. Subsequent etherification of the free OH groups makes it possible to prepare the desired triazine derivatives may be prepared in a two-step reaction.

Accordingly, this invention relates to symmetrical triazine derivatives of formula

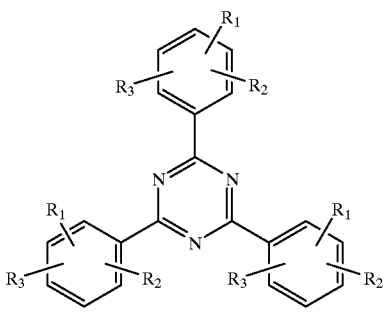

(1)

wherein
$R_1$ and $R_2$ are each independently of the other hydrogen; $C_1$–$C_{12}$alkyl; or $C_1$–$C_{12}$alkoxy; and $R_3$ is $C_1$–$C_{12}$alkyl; or $C_1$–$C_{12}$alkoxy.

$C_1$–$C_{12}$Alkyl or $C_1$–$C_{12}$alkoxy are straight-chain or branched alkyl radicals, typically methyl, ethyl, n-propyl, isopropyl, n-butyl, sec-butyl, tert-butyl, amyl, isoamyl or tert-amyl, heptyl, octyl, isooctyl, nonyl, decyl, undecyl or dodecyl, or methoxy, ethoxy, propoxy, butoxy, pentyloxy, hexyloxy, heptyloxy, octyloxy, nonyloxy, decyloxy, undecyloxy or dodecyloxy.

Particularly preferred compounds are those of formula (1), wherein
$R_3$ is $C_1$–$C_{12}$alkoxy, in particular $C_5$–$C_{12}$alkoxy; and
$R_1$ and $R_2$ have the meaning given in formula (1).

Very particularly preferred compounds are those conforming to formula

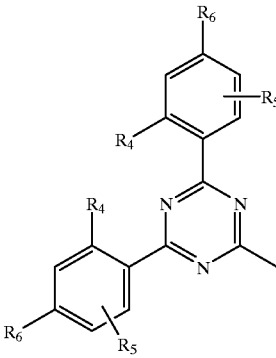

(2)

wherein
$R_4$ and $R_5$ are each independently of the other hydrogen; $C_1$–$C_{12}$alkyl; or $C_1$–$C_{12}$alkoxy; and
$R_6$ is $C_1$–$C_{12}$alkyl; or $C_1$–$C_{12}$alkoxy.

Important compounds are, in particular, those of formula (2), wherein
$R_4$ is hydrogen; and
$R_5$ and $R_6$ are $C_5$–$C_{12}$alkoxy;
or those compounds of formula (2), wherein
$R_4$ and $R_5$ are $C_5$–$C_{12}$alkyl; and
$R_6$ is hydrogen.

Very particularly preferred compounds are those of formula

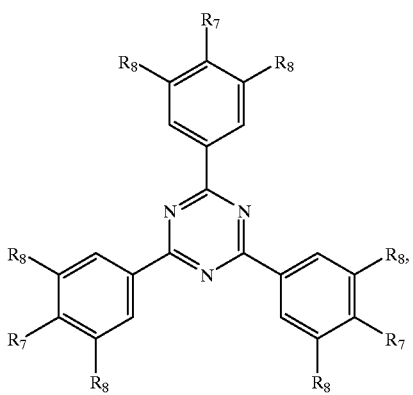

(3)

wherein $R_7$ is $C_5$–$C_{12}$alkoxy; and $R_8$ is hydrogen; or $C_1$–$C_5$alkyl.

The triazine derivatives of this invention can be used as single compounds or as mixtures of different single compounds with each other.

The novel symmetrical triazine derivatives of formula (1) can, in particular, also be used as mixtures with triazine compounds of formula

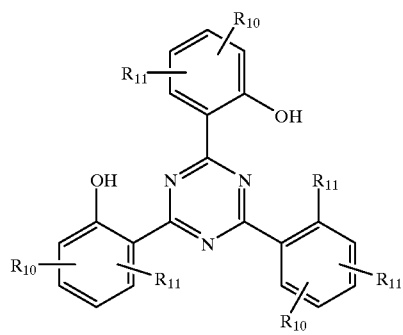

(4)

In formula (4), $R_{10}$ is hydrogen; $C_6$–$C_{12}$alkyl; or $C_2$–$C_6$alkenyl; and $R_{11}$ is $C_1$–$C_{12}$alkoxy.

$C_2$–$C_6$Alkenyl is, for example, allyl, methallyl, isopropenyl, 2-butenyl, 3-butenyl, isobutenyl, n-penta-2,4-dienyl or 3-methyl-but-2-enyl.

The mixtures of triazine compounds of formula (1) and formula (4) are another subject matter of this invention.

The novel triazine derivatives of formula (1) may be prepared in different manner. In a Grignard reaction, for example, 1 mol of cyanuric chloride is reacted with 3 mol of the corresponding phenylmagnesium bromide compound which, depending on the meaning of $R_1$, $R_2$ and $R_3$ of formula (1), may contain an alkyl radical and/or one or several free hydroxyl groups. Processes for the preparation of this intermediate are known and are described, inter alia, in EP-A-0,557,559.

This intermediate is also obtainable by Friedel-Crafts alkylation of cyanuric chloride with the corresponding phenyl compounds which, depending on the meaning of $R_1$, $R_2$ and $R_3$ in formula (1), may contain an alkyl radical and/or one or several free hydroxyl groups, in the presence of a Lewis acid, preferably aluminium chloride.

According to A. Ninagawa, M. Kawazoe, H. Matsuada, Makromol.Chem. 180, (1979), 2123, this intermediate is also obtainable by cyclotrimerisation of a benzonitrile compound containing an alkyl radical and/or one or more than one hydroxyl group, depending on the meaning of $R_1$, $R_2$ and $R_3$ in formula (1).

The end products corresponding to formula (1) are obtainable in a second reaction step by etherifying the hydroxyl group of the intermediates obtained in the first reaction step by alkylation in accordance with customary methods.

A further subject matter of this invention relates to the processes for the preparation of the novel triazine derivatives.

The inventive symmetrical triazine derivatives of formula (1) or mixtures of these compounds with triazine compounds of formula (4) as well as compounds of formula

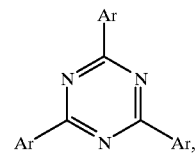

(5)

wherein

Ar is a radical of formula

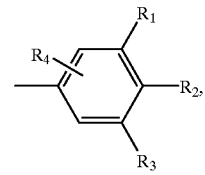

(5a)

$R_1$ is hydrogen; hydroxy; $C_1$–$C_{12}$alkyl; or $C_1$–$C_{12}$alkoxy;

$R_2$ is hydroxy; $C_1$–$C_{12}$alkoxy; or benzyloxy;

$R_3$ is hydroxy; $C_1$–$C_{12}$alkyl; or $C_1$–$C_{12}$alkoxy; and $R_4$ is hydrogen; or $C_1$–$C_{12}$alkoxy; or $R_1$ and $R_2$, together with the phenyl radical, are a heterocyclic five-membered ring which is condensed with benzene, preferably a radical of formula (5a)

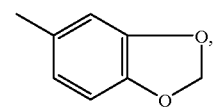

are particularly suitable as UV filters, i.e. for protecting ultraviolet-sensitive organic materials, in particular the skin and hair of humans and animals, against the harmful effects of UV radiation.

Illustrative examples of compounds of formula (5) are

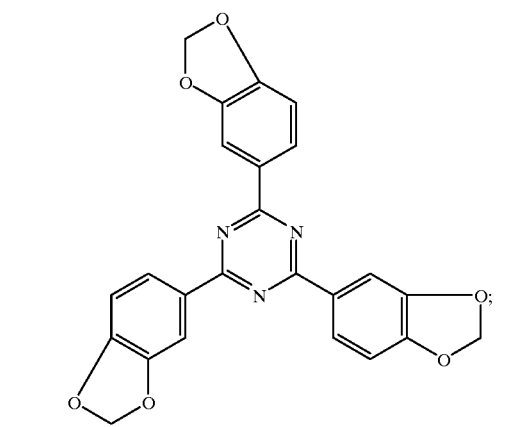

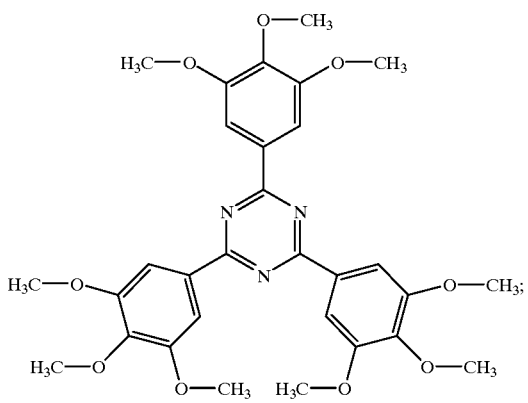

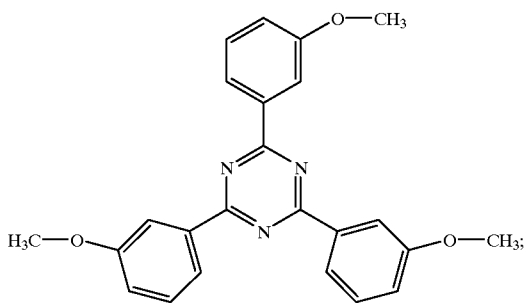

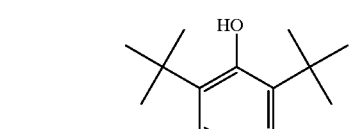

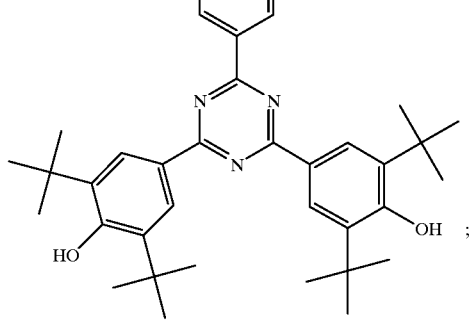

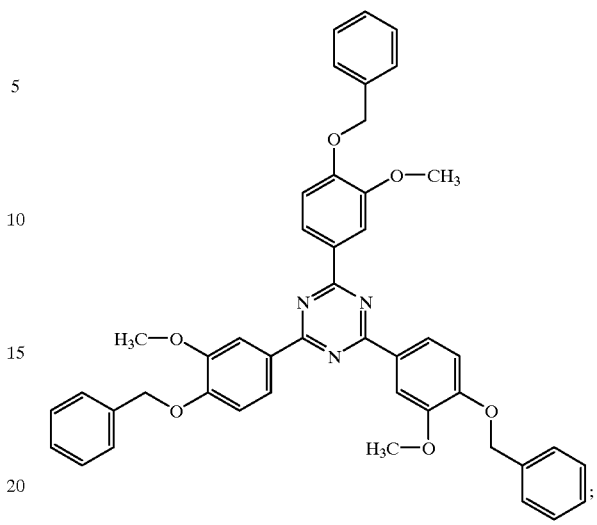

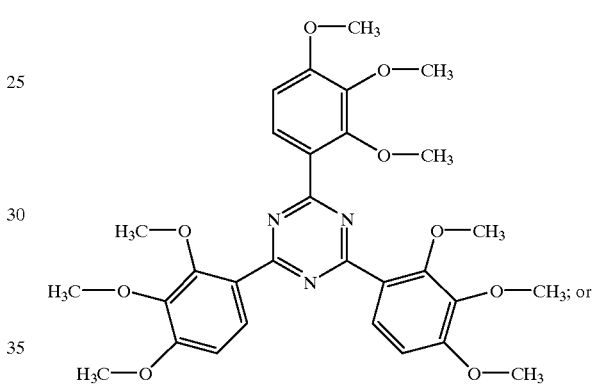

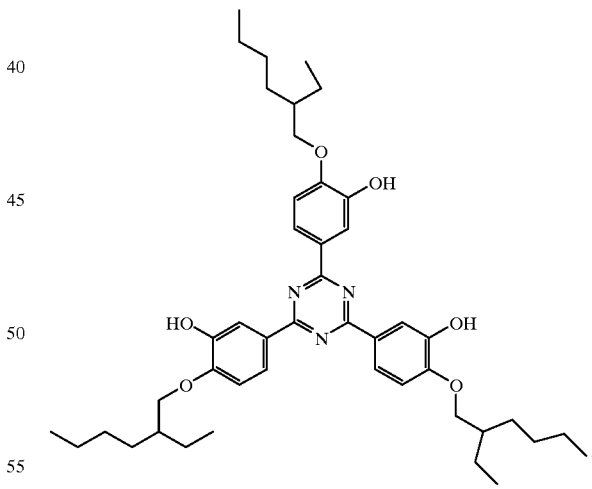

Accordingly, these compounds are suitable as light stabilisers in cosmetic, pharmaceutical and veterinary preparations. They can be obtained in dissolved form or, it they are only sparingly soluble or insoluble, they can be incorporated in the preparations in micronised form having an average particle size in the range of 0.02 to 2, preferably of 0.05 to 1.5 and, most preferably, of 0.1 to 1.0 μm.

Accordingly, another object of this invention is the provision of a cosmetic preparation for skin or hair, which comprises at least one compound of formula (1) or (5) as well as carriers or auxiliaries which are cosmetically compatible with skin and hair, or to a cosmetic formulation for skin or hair, which comprises a mixture of a) at least one or more than one compound of formula (1) or (5), and b) a compound of formula (4)

together with carriers or auxiliaries which are cosmetically compatible with skin and hair.

In addition to the novel UV absorbers, the cosmetic formulations can also contain one or more than one further UV protective of the following substance classes:

1. p-aminobenzoic acid derivatives, typically 2-ethylhexyl 4-dimethylaminobenzoate;
2. salicylic acid derivatives, typically 2-ethylhexyl salicylate;
3. benzophenone derivatives, typically 2-hydroxy-4-methoxybenzophenone and its 5-sulfonic acid derivative;
4. dibenzoylmethane derivatives, typically 1-(4-tert-butylphenyl)-3-(4-methoxyphenyl)-propane-1,3-dione;
5. diphenylacrylates, typically 2-ethylhexyl-2-cyano-3,3-diphenylacrylate and 3-(benzo-furanyl)-2-cyanoacrylate;
6. 3-imidazol-4-yl-acrylic acid and 3-imidazol-4-yl-acrylate;
7. benzofuran derivatives, preferably 2-(p-aminophenyl) benzofuran derivatives, disclosed in EP-A-582,189, U.S. Pat. No. 5,338,539, U.S. Pat. No. 5,518,713 and in EP-A-613,893;
8. polymeric UV absorbers, such as the benzylidenemalonate derivatives described, inter alia, in EPA-709,080;
9. cinnamic acid derivatives, typically the 2-ethylhexyl 4-methoxycinnamate or isoamylate or cinnamic acid derivatives disclosed, inter alia, in U.S. Pat. No. 5,601,811 and WO 97/00851;
10. camphor derivatives, typically 3-(4'-methyl) benzylidenebornan-2-one, 3-benzylidene-bornan-2-one, N-[2(and 4)-2-oxyborn-3-ylidenemethyl)benzyl] acrylamide polymer, 3-(4'-trimethylammonium) benzylidenebornan-2-one methyl sulfate, 3,3'-(1,4-phenylenedime-thine)-bis (7,7-dimethyl-2-oxo-bicyclo-[2.2.1]heptane-1-methansulfonic acid) and the salts thereof, 3-(4'-sulfo)benzylidenebornan-2-one and the salts thereof;
11. trianilino-s-triazine derivatives, typically 2,4,6-trianiline-(p-carbo-2'-ethyl-1'-oxi)-1,3,5-triazines as well as the UV absorbers disclosed in U.S. Pat. No. 5,332,568, EP-A-517,104, EP-A-507,691, WO 93/17002 and EP-A-570,838;
12. 2-hydroxyphenylbenzotriazole derivatives;
13. 2-phenylbenzimidazole-5-sulfonic acid and the salts thereof;
14. menthyl-o-aminobenzoate;
15. $TiO_2$ (coated differently), ZnO and mica.

The UV absorbers described in "Sunscreens", Eds. N. J. Lowe, N. A.Shaath, Marcel Dekker, Inc., New York and Basel or in Cosmetics & Toiletries (107), 50 et seq. (1992), can also be used as additional UV protectives in the inventive formulations.

The cosmetic formulations can also be used together with known antioxidants, such as vitamin E, carotinoids or HALS compounds.

The novel cosmetic formulations usually comprise 0.1 to 25, preferably 0.5 to 10%, by weight, based on the total weight of the formulation, of a UV absorber of formula (1) or (5) or of a mixture of UV absorbers of formula (1) and formula (4) and a cosmetically compatible auxiliary.

The cosmetic formulations can be prepared by physically mixing the UV absorber(s) with the auxiliaries by conventional methods, such as by simply stirring the individual components together.

The cosmetic formulations of this invention can be formulated as water-in-oil or oil-in-water emulsion, as oil-in-alcohol lotion, as vesicular dispersion of a ionic or nonionic amphiphilic lipid, as gel, solid stick or as aerosol formulation.

As water-in-oil or oil-in-water emulsion, the cosmetically compatible auxiliary preferably comprises 5 to 50% of an oil phase, 5 to 20% of an emulsifier and 30 to 90% of water. The oil phase can contain any oil suitable for cosmetic formulations, for example one or several hydrocarbon oils, wax, natural oil, silicone oil, fatty acid ester or fatty alcohol. Preferred mono- or polyols are ethanol, isopropanol, propylene glycol, hexylene glycol, glycerol and sorbitol.

Cosmetic formulations for hair can be present in the form of a shampoo, lotion, gel or emulsion for rinsing, before or after shampooing, before or after dyeing or removing dye, before or after a perming or straightening process, in the form of a lotion, foam or gel for setting or treating hair, in the form of a lotion or gel for brushing or waving hair, in the form of a hair lacquer, in the form of a composition for perming or straightening hair, for dyeing or removing dye.

It is possible to use, for example, the following cosmetic formulations for hair:

$a_1$) spontaneously emulsifying stock formulations, consisting of the UV absorber, PEG-6 $C_{10}$oxoalcohol and sorbitan esquioleate, which is charged with water and any quaternary ammonium compound, such as 4% minkamidopropyidimethyl-2-hydroxyethyl ammonium chloride or Quaternium 80;

$a_2$) spontaneously emulsifying stock formulation, consisting of the UV absorber, tributyl citrate and PEG-20 sorbitan monooleate, which is charged with water and any quaternary ammonium compound, such as 4% minkamidopropyldimethyl-2-hydroxyethyl ammonium chloride or Quaternium 80;

b) quat-doped solutions of the UV absorber in butyl triglycol and tributyl citrate;

c) dispersions of micronised UV absorbers obtained by known methods (precipitation from solutions or mixtures of solutions, grinding), having an average diameter of 0.05–1.0 $\mu$m in APG (e.g. Plantaren), and a quat (e.g. minkamidopropyldimethyl-2-hydroxyethyl ammonium chloride) in an aqueous formulation;

d) mixtures or solutions of the UV absorber with n-alkylpyrrolidone.

The cosmetic formulations for skin or hair may also contain other components, such as emollients, emulsion stabilisers, skin moisturisers, suntan promoters, thickeners, such as xanthan, moisture retention agents, such as glycerol, preservatives, fragrances and colourants.

The novel cosmetic formulations for skin or hair are distinguished by excellently protecting human skin and hair against the harmful effects of sunlight.

The following non-limitative Examples illustrate the invention in more detail. Percentages are by weight.

EXAMPLE 1

Preparation of 2,4,6-tris(4-2-ethylhexyloxyphenyl)-(1,3,5)-triazine

The basic structure of formula

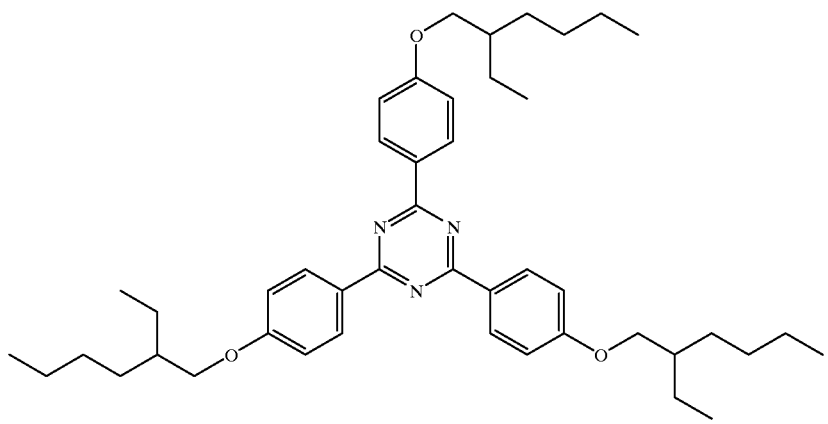

(101)

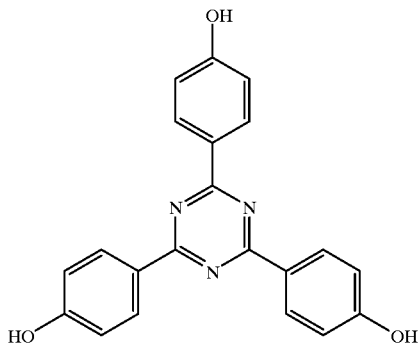

(101a)

is prepared by cyclotrimerising p-hydroxybenzonitrile according to A. Ninagawa, M. Kawazoe, H. Matsuda, Makromol. Chem. 180 (1979), 2123.

5.36 g of the compound of formula (101a) are dissolved in 50 ml of dimethylformamide (DMF) and are charged with 6.53 g of finely powdered potassium carbonate at 100–105° C. This mixture is stirred for 30 minutes and then 8.23 g of 3-(chloromethyl)heptane, dissolved in 10 ml of DMF, are added dropwise over another 30 minutes at 100–105° C. The temperature is slowly elevated to 135° C. over 6 hours. After cooling to 100° C., 50 ml of toluene are added and the precipitated salts are removed by filtration. The filtrate is concentrated to dryness by evaporation and the residue is taken up with 50 ml of toluene and 100 ml of water, acidified and extracted by shaking. The dried organic phase is concentrated by evaporation. The crude product (c. 7 g) is purified by column chromatography (silica gel, cyclohexane/toluene 7:3).

Yield: 4.8 g of colourless oil (46% of theory).

EXAMPLE 2

Preparation of 2,4,6-tris[3,5-dimethyl-4-(2-ethylhexyloxyphenyl)-(1,3,5)-triazine

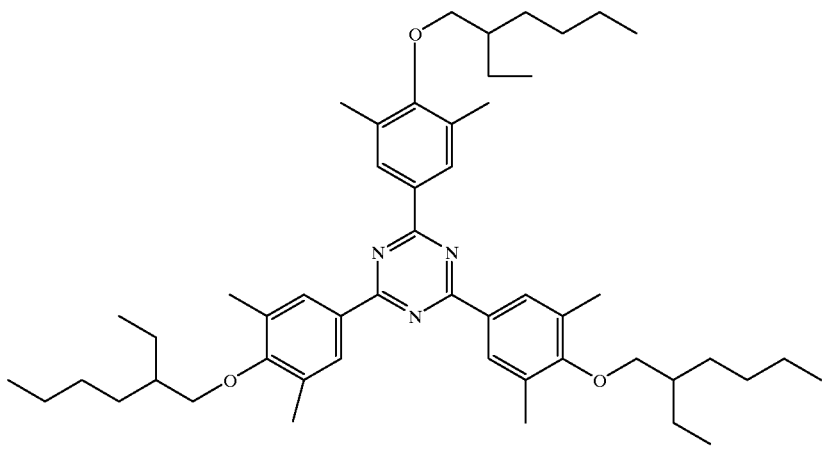

(102)

The basic structure of formula (102a)

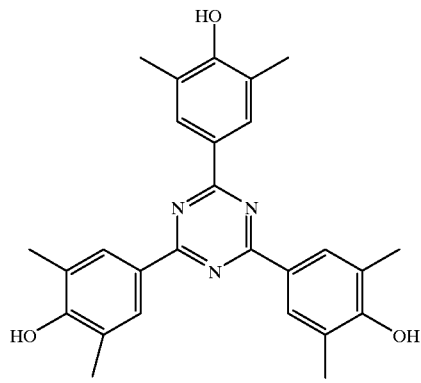

is obtained, for example, by reacting 2,6-dimethylphenol with cyanuric chloride under Friedel-Crafts conditions (cf DE-A-2,219,012).

6.62 g of the compound of formula (102a) are dissolved in 70 ml of dimethylformamide and are charged with 6.53 g of finely powdered potassium carbonate at 100–105° C. This mixture is stirred for 30 minutes and then 11.65 g of 3-(chloromethyl)heptane, dissolved in 10 ml of DMF, are added dropwise over another 60 minutes at 100–105° C. The temperature is kept at 100–105° C. for 3 hours. After cooling to 100° C., 50 ml of toluene are added and the precipitated salts are removed by filtration. The filtrate is concentrated to dryness by evaporation and the residue is charged with 100 ml of toluene and 100 ml of water, acidified and extracted by shaking. The organic phase is washed with water until neutral, separated, dried and concentrated by evaporation. The crude product (c. 10 g) is purified by column chromatography (silica gel, cyclohexane/toluene 65:35).

Yield: 4.7 g of colourless crystals, m.p. 83–84° C., (40% of theory).

EXAMPLE 3

The compounds of formula (103)

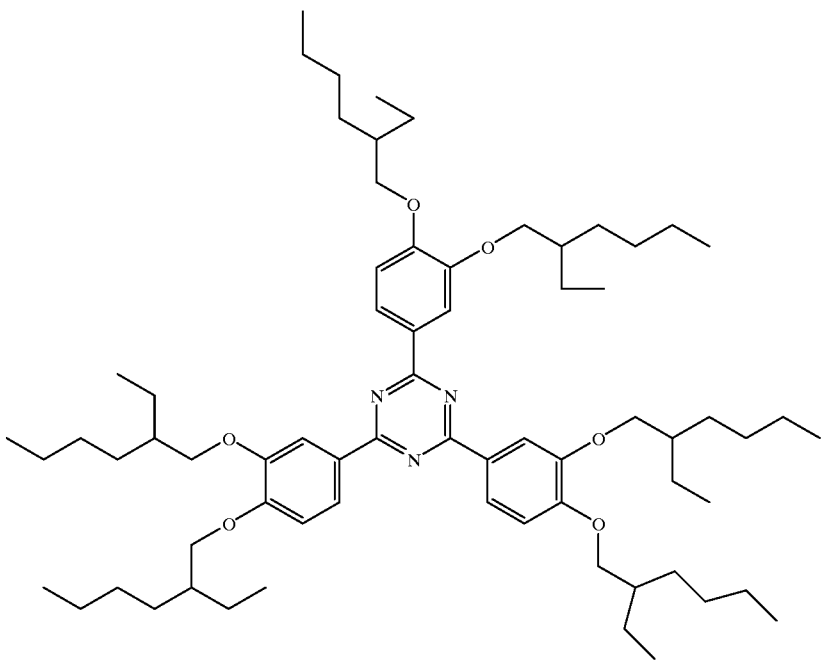

can be prepared in general analogy to the procedure of Example 1.

USE EXAMPLES

EXAMPLE 4

Preparation of an O/W emulsion

Formulation (names according to CTFA or INCI):

| | | |
|---|---|---|
| ($a_1$) | ceteareth 6 (and) stearyl alcohol | 2.0% |
| ($a_2$) | ceteareth 25 | 2.0% |
| ($a_3$) | cetearyl alcohol | 5.0% |
| ($a_4$) | caprylic/capric triglyceride | 5.0% |
| ($a_5$) | cetearyl octanate | 10.0% |
| ($a_6$) | Vaseline | 5.0% |
| ($a_7$) | compound of formula (101) | 4.0% |
| ($b_1$) | propylene glycol | 3.0% |
| ($b_2$) | carbopol 934 | 0.2% |
| ($b_3$) | $H_2O$ | 63.53% |
| (c) | triethanol amine | 0.27% |

Components ($a_1$)–($a_7$) (=phase A) and ($b_1$)–($b_3$) (=phase B) are heated to 75–80° C. Phase B is then added to phase A and homogenised. Component (c) (=phase C) is then added and again homogenised.

The sunscreen factors are determined by the method of Diffey and Robson, J. Soc. Cosmet. Chem. 40, 127–133 (1989) using an SPF (sunproof factor) analyser (Optometrix, SPF 290).

This O/W emulsion has a sunscreen factor of 7.8.

EXAMPLE 5

Preparation of a Suntan Cream

Formulation (the individual components are named according to CTFA or INCI):

| | Phase A: | |
|---|---|---|
| ($a_1$) | dimethicone | 2.0% |
| ($a_2$) | isopropyl myristate | 9.0% |
| ($a_3$) | stearyl alcohol | 10.0% |
| ($a_4$) | stearic acid | 4.0% |
| ($a_5$) | compound of formula (102) | 4.0% |
| ($a_6$) | micronised 2,4-bis(phenyl)-6-(2-hydroxy-4-methoxyphenyl)-(1,3,5)-triazine (Ø 0.25 µm) | 3.2% |
| ($b_1$) | triethanol amine | 1.2% |
| ($b_2$) | carbomer 934 (1%) | 5.0% |
| ($b_3$) | $H_2O$ | 61.6% |

Components ($a_1$–$a_6$) (=phase A) are homogenised separately and very carefully and are then, like components ($b_1$)–($b_3$) (=phase B), heated separately to 75–80° C. Phase B is then added to phase A with vigorous stirring. With stirring, the mixture is allowed to cool.

This suntan cream has a sunscreen factor of 11.

What is claimed is:

1. A compound of formula

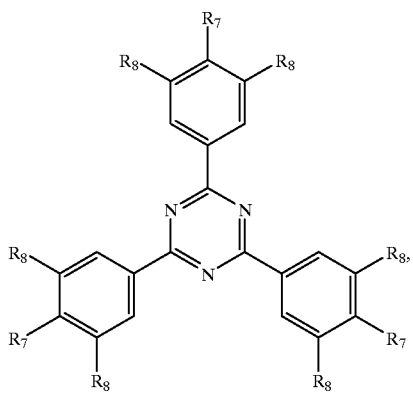
(3)

wherein
$R_7$ is $C_5$–$C_{12}$alkoxy; and
$R_8$ is $C_1$–$C_5$alkyl.

2. A mixture of the compounds of formula (3) according to claim 1 and of formula

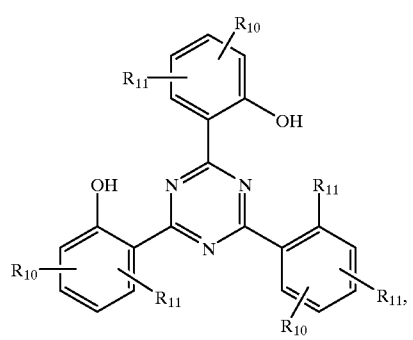
(4)

wherein
$R_{10}$ is hydrogen; $C_6$–$C_{12}$alkyl; or $C_2$–$C_6$alkenyl; and
$R_{11}$ is $C_1$–$C_{12}$alkoxy.

3. A process for the preparation of a compound of the formula (3)

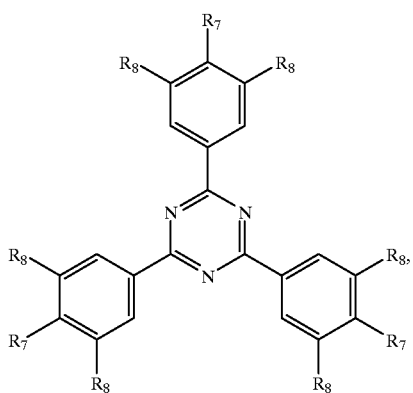
(3)

wherein $R_7$ is $C_5$–$C_{12}$alkoxy; and
$R_8$ is hydrogen; or $C_1$–$C_5$alkyl, which comprises reacting in a first reaction step 1 mole of cyanuric chloride with 3 moles of a phenyl compound of the formula

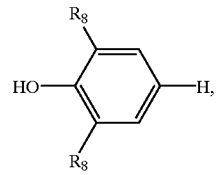

wherein $R_8$ is hydrogen; or $C_1$–$C_5$alkyl, by Friedel-Crafts alkylation in the presence of a Lewis acid and, in a second reaction step, etherifying the free hydroxyl groups in an alkylation reaction.

4. A process for the preparation of a compound of the formula (3)

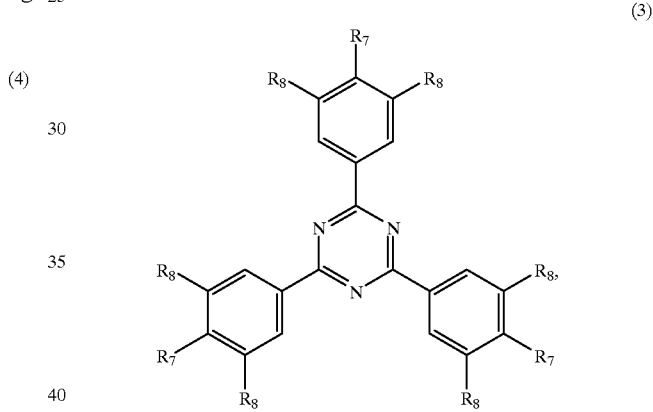
(3)

wherein $R_7$ is $C_5$–$C_{12}$alkoxy; and
$R_8$ is hydrogen; or $C_1$–$C_5$alkyl, which comprises cyclotrimerising in a first reaction step a benzonitrile compound of the formula

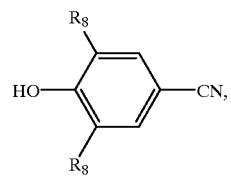

wherein $R_8$ is hydrogen; or $C_1$–$C_5$alkyl, and, in a second reaction step, etherifying the free hydroxyl groups in an alkylation reaction.

5. A method of protecting human and animal hair and skin from the harmful effects of UV radiation which comprises contacting the hair and skin with an effective amount of a compound of formula

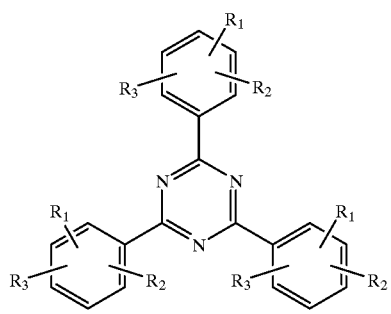

(1)

wherein
$R_1$ and $R_2$ are each independently of the other hydrogen, $C_1$–$C_{12}$alkyl, $C_1$–$C_{12}$alkoxy; and
$R_3$ is $C_1$–$C_{12}$alkyl; or $C_1$–$C_1$alkoxy, or

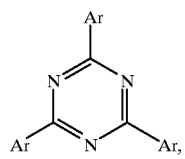

(5)

wherein
Ar is a radical of formula

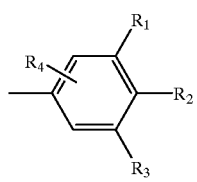

(5a)

$R_1$ is hydrogen; hydroxy; $C_1$–$C_{12}$alkyl; or $C_1$–$C_{12}$alkoxy;
$R_2$ is hydroxy; $C_1$–$C_{12}$alkoxy; or benzyloxy;
$R_3$ is hydroxy; $C_1$–$C_{12}$alkyl; or $C_1$–$C_{12}$alkoxy; and
$R_4$ is hydrogen; or $C_1$–$C_{12}$alkoxy; or
$R_1$ and $R_2$, together with the phenyl radical, are a heterocyclic five-membered ring which is condensed with benzene.

6. A cosmetic preparation for skin or hair, comprising at least one or more than one compound of formula (1) or (5) as defined in claim 5 together with carriers or auxiliaries which are cosmetically compatible with hair and skin.

7. A cosmetic preparation for skin or hair, comprising a mixture of a) at least one compound of formula (1) or (5) as defined in claim 5, and
b) a compound of formula

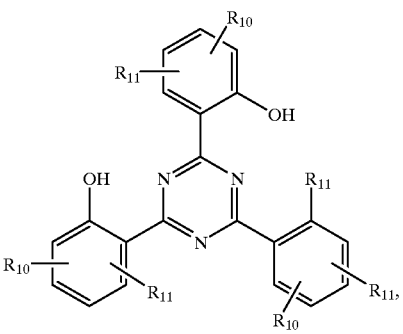

(4)

wherein
$R_{10}$ is hydrogen: $C_6$–$C_{12}$alkyl: or $C_2$–$C_6$alkenyl; and
$R_{11}$ is $C_1$–$C_{12}$alkoxy,
together with carriers or auxiliaries which are cosmetically compatible with hair and skin.

8. A cosmetic preparation for skin or hair according to claim 7, which comprises at least 0.1 to 25% by weight, based on the total weight of the formulation, of a UV absorber of formula (1) or (5) or of a mixture of UV absorbers of formula (1) and of formula (4) as well as at least one auxiliary which is compatible with skin and hair.

9. The compound according to claim 1, wherein $R_7$ is 2-ethylhexyl and $R_6$ is methyl.

10. A cosmetic preparation for skin or hair, comprising at least one compound of formula (3) as defined in claim 1 together with carriers or auxiliaries which are cosmetically compatible with hair and skin.

11. A process for treating human hair to protect it from the harmful effects of UV radiation, which comprises treating the hair with a shampoo, lotion, gel or emulsion for rinsing, before or after shampooing, before or after dyeing or removing the dye, before or after a perming or straightening process, with a lotion, foam or gel for setting, with a lotion, foam or gel for brushing or waving, with a hair lacquer, with a composition for perming or straightening hair, for dyeing or removing dye, which shampoo, lotion, gel, emulsion, foam, hair lacquer or composition for perming, straightening, dyeing or removing dye comprises at least one UV absorber of formula (1) or (5) or a mixture of a UV absorber of formula (1) and of formula (4) as defined in claim 7.

* * * * *

UNITED STATES PATENT AND TRADEMARK OFFICE
CERTIFICATE OF CORRECTION

PATENT NO. : 6,217,856 B1  
DATED : April 17, 2001  
INVENTOR(S) : Thomas Ehlis et al.

Page 1 of 1

It is certified that error appears in the above-identified patent and that said Letters Patent is hereby corrected as shown below:

<u>Column 17,</u>  
Line 19, should read:  
-- $R_3$ is $C_1$-$C_{12}$alkyl; or $C_1$-$C_{12}$alkoxy, or --.

Signed and Sealed this

Fifth Day of March, 2002

*Attest:*

*Attesting Officer*

JAMES E. ROGAN  
*Director of the United States Patent and Trademark Office*